United States Patent [19]

Roebke

[11] 4,065,569

[45] Dec. 27, 1977

[54] USE OF 2-IMIDAZOLINES AS HYPOGLYCEMIC AGENTS

[75] Inventor: Heide Roebke, Belleville, N.J.

[73] Assignee: Schering Corporation, Kenilworth, N.J.

[21] Appl. No.: 717,800

[22] Filed: Aug. 25, 1976

Related U.S. Application Data

[63] Continuation of Ser. No. 582,313, May 30, 1975, Pat. No. 3,992,403.

[51] Int. Cl.$^2$ ............................................. A61K 31/415
[52] U.S. Cl. ................................................ 424/273 R
[58] Field of Search ........................................... 424/273

[56] References Cited

U.S. PATENT DOCUMENTS

| | | | |
|---|---|---|---|
| 2,778,836 | 1/1957 | Morren | 260/309.6 X |
| 2,948,724 | 8/1960 | Sahyun et al. | 260/309.6 X |
| 2,948,749 | 1/1960 | Buckley et al. | 260/309.6 X |

*Primary Examiner*—Frederick E. Waddell
*Attorney, Agent, or Firm*—Stephen B. Coan; Raymond A. McDonald; Bruce M. Eisen

[57] ABSTRACT

The present 2-substituted imidazolines possess valuable hypoglycemic activity. The compounds are prepared by the condensation of an appropriately substituted aryl nitrile with a diamine.

11 Claims, No Drawings

USE OF 2-IMIDAZOLINES AS HYPOGLYCEMIC AGENTS

This application is a continuation application of application Ser. No. 582,313, filed May 30, 1975 now U.S. Pat. No. 3,992,403, issued on Nov. 16, 1976.

This invention relates to compositions of matter classified in the art of chemistry as imidazolines, and to the process for making and using such compositions.

The invention sought to be patented in one of its process aspects resides in the conversion of certain amidines and imidates to the desired imidazolines by reaction with an appropriate diamine. Another process aspect sought to be patented is the pyrolysis of a nitrile with an acid salt of an appropriate diamine.

The invention, in still another of its process aspects, resides in the method of effecting a hypoglycemic effect in warm-blooded animals by administering a therapeutically effective quantity of a composition of matter of this invention.

More particularly, this invention relates to the novel compositions of matter having the general structural formula:

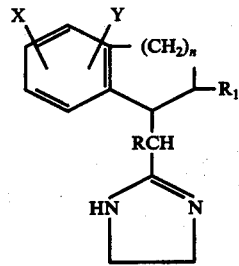

I and the pharmaceutically acceptable acid addition salts thereof, wherein each of X and Y are hydrogen or fluoro, each of R and $R_1$ are lower alkyl or hydrogen, and $n$ is an integer 1 to 3.

As used herein, "lower alkyl" refers to straight, branched-chain and cyclized hydrocarbyl radicals having up to six carbon atoms, preferably methyl, but also including ethyl, isopropyl, propyl, n-butyl, t-butyl, cyclopropyl, cyclohexyl and the like. In those instances wherein $n$ represents 1, the structure represents a 2-[1-indanylmethyl]-2-imidazoline, when $n$ is 2, the structure represents a 2-[(1,2,3,4-tetrahydro-1-naphthyl)methyl]-2-imidazoline, and when $n$ is 3, the structure represents a 2-[6,7,8,9-tetrahydro-5H-5-benzocycloheptenyl methyl]-2-imidazoline.

Pharmaceutically acceptable acid addition salts of the compounds of this invention are such salts formed with inorganic acids as hydrochloric, hydrobromic, sulfuric, phosphoric and the like acids, or with organic acids, such as organic carboxylic acids, e.g., formic, acetic, propionic, glycolic, malonic, succinic, maleic, fumaric, malic, tartaric, citric, benzoic, cinnamic, salicylic, 4-aminosalicylic, 2-phenoxybenzoic, 2-acetoxybenzoic acid and the like, or organic sulfonic acids, e.g. methane sulfonic, ethane sulfonic, 2-hydroxyethane sulfonic, ethane 1,2-di-sulfonic, benzene sulfonic, p-toluene sulfonic, naphthalene-2-sulfonic acid and the like. Other acid addition salts are used as intermediates, for example, in the purification of the free bases or in the preparation of other, for example, pharmaceutically acceptable acid addition salts, as well as for identification and characterization purposes. Acid addition salts, which are primarily used for the latter are, for example, those with certain inorganic acids, e.g., perchloric acid and the like, with acidic organic nitro compounds, e.g., picric, picrolonic, flavianic acid and the like, or with metal complex acids, e.g. phosphotungstic, phosphomolybdic, chloroplatinic, Reinecke acid, and the like.

The compounds of this invention may be prepared from appropriately substituted nitriles by a series of analogously known methods. In a preferred method, an appropriately substituted nitrile (II) is condensed with a diamine (III) by heating the reactants together in the presence of a catalyst, such as sulfur, at temperatures of about 100°-200° C. The reaction is effected in the atmosphere of an inert gas such as nitrogen. The heating is generally continued for about 2-10 hours, although the reaction may take up to 24 hours. This reaction may be depicted by the following reaction scheme:

Reaction Scheme A

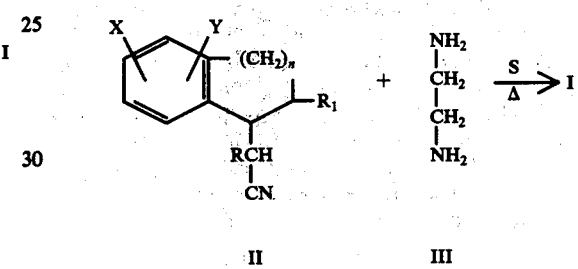

wherein X, Y, R, $R_1$ and $n$ are as defined in formula I. Alternatively, the diamine (III) reactant may be used in the form of their sulfonic acid salts to yield derivatives which, upon neutralization, yield the desired product (I). For example, by the employment of an ethylene diamine tosylate and by effecting the foregoing reaction, there is produced the appropriate imidazoline tosylate, which product, by standard techniques wellknown in the art, e.g., reaction with sodium hydroxide, is converted to the desired base (I).

Alternatively, the desired products (I) may be prepared from the appropriately substituted nitriles (II) by first forming an intermediate which is then heated with the diamine reactant to form the desired product (I). For example, by reacting the nitrile (II) with hydrogen sulfide, or an equivalently functioning sulfide, an appropriately substituted thioamide intermediate (IV) is formed which, when heated with a diamine (III) produces the desired product (I). In effecting this modified condensation reaction, the reactants are preferably reacted in the presence of a basic catalyst, such as, triethylamine or N-methyl-piperidine, in an inert organic solvent such as dimethylformamide, pyridine, and the like. Preferably, the triethylamine is used in excess quantities. This set of reactions may be depicted by the following reaction scheme:

Reaction Scheme B

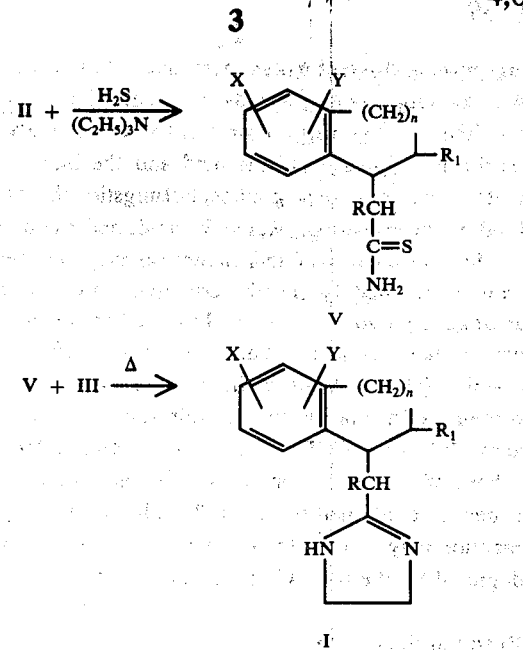

wherein X, Y, R, $R_1$ and n are as previously defined.

In essence, the foregoing reaction scheme represents a reactive derivative which is the functional equivalent of the cyano group (of formula II). Other such functionally equivalent reactive groups are imido-ethers, preferably in the form of their hydrohalic salts, imido-thioethers, imido halides, amidino, and thiamido groupings, and the like. These equivalently functioning groups may be represented by the formulae:

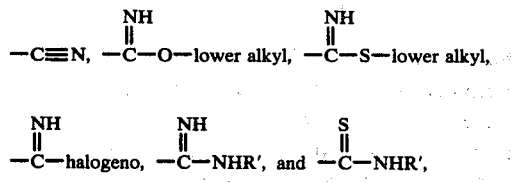

wherein halogeno preferably represents chloro or bromo, and R' represents lower alkyl or hydrogen.

In general, the intermediate nitriles of formula II are known compounds, however, in those instances wherein a particular nitrile is unknown, then the preparation of such intermediary nitriles is readily effected by standard and analogously known procedures wherein the appropriate aryl alkyl ketone is condensed with a cyanomethyl Wittig reagent, preferably diethyl cyanomethylphosphonate. Specifically, the condensation is carried out with sodium hydride in an alkyl ether solvent, e.g. dimethoxyethane under a nitrogen atmosphere at the reflux temperature of the reaction mixture. The unsaturated nitriles thus obtained are converted to the nitriles II by catalytic hydrogenation. Specifically, this reaction is carried out using a catalyst such as 5% palladium on charcoal in a solvent such as ethyl acetate under 2-4 atmospheres of hydrogen.

From an inspection of the structure of the compounds, it is quite obvious that some of the compounds will exist as geometrical isomers of one another (e.g. cis- and trans-) and others will exist as stereo isomers of one another (e.g. dextro and levo). In those instances wherein such isomerism exists, both forms, and mixtures thereof, are contemplated herein. Standard techniques for the separation of such isomers (or for the preparation of the specifically desired isomers by the choice of the proper form of the reactant), may be utilized in the event one form or another is desired. Indications are, however, that both forms are equally effective.

The following examples illustrate the above-described methods for the preparation of compounds embraced by this invention. Such exemplifications, while particularizing the details of the chemical processes of this invention, are not to be construed as limiting the scope of the inventive concepts herein described.

EXAMPLE 1

2-[(6-Fluoro-1,2,3,4-tetrahydro-1-naphthyl)-methyl]-2-imidazoline hydrochloride

Part A

To a mixture of 7.2 g. (0.3 mole) of sodium hydride in 350 ml. of dimethoxyethane under a nitrogen atmosphere add in a dropwise fashion 53.1 g (0.3 mole) of diethyl cyanomethylphosphonate, maintaining the temperature at 25°-30° during the addition. After stirring the reaction mixture for 1.5 hours, slowly add 24.6 g. (0.2 mole) of 6-fluoro-3,4-dihydro-1(2H)-naphthalenone and stir the resulting mixture at room temperature for 0.5 hours then at reflux for 2 hours. Cool the mixture, add water and isolate the product with ether. Purify the crude 6-fluoro-1,2,3,4-tetrahydro-$\Delta^{1(2H),\alpha}$-naphthaleneacetonitrile by distillation.

Hydrogenate a mixture containing 18.7 g. (0.1 mole) of the above nitrile and 4 g. of 5% palladium on charcoal in 200 ml. of ethyl acetate under 4 atmospheres of hydrogen for 2 days. Filter the mixture, remove the solvent and distil the remaining oil to give 6-fluoro-1,2,3,4-tetrahydro-1-naphthalene-acetonitrile.

Part B

Saturate a solution of 15 g. of 6-fluoro-1,2,3,4-tetrahydro-1-naphthaleneacetonitrile and 15 ml. of anhydrous methanol in 75 ml. of anhydrous ether with HCl at 0°. Keep at 0° for 18 hours, add additional ether to precipitate the imino ether hydrochloride, and filter to isolate the product.

Add 5 g. of ethylenediamine to a solution of the above isolated imino ether hydrochloride in 100 ml. of methanol. Heat at reflux for 3 days, then cool and acidify with ethanolic HCl, filter to remove unreacted ethylenediamine dihydrochloride, concentrate the filtrate, recrystallize the residue from acetonitrile to give 2-[(6-fluoro-1,2,3,4-tetrahydro-1-naphthyl)-methyl]-2 -imidazoline hydrochloride.

EXAMPLE 2

2-[(1,2,3,4-Tetrahydro-1-naphthyl)-methyl]-2-imidazoline hydrochloride

Saturate a solution of 9.3 g. of (1,2,3,4-tetrahydro-1-naphthalene)-acetonitrile and 10 ml. anhydrous methanol in 50 ml. of anhydrous ether with HCl at 0°. Keep at 0° for 18 hours, add additional ether to precipitate the iminoether hydrochloride, and filter, m.p. 113°-114° C.

Add 1.7 g. ethylenediamine to a solution of 6.0 g. of the iminoether hydrochloride in 50 ml. methanol with cooling. Heat at reflux for 3 days, then cool and acidify with ethanolic HCl, filter remove ethylenediamine dihydrochloride. Concentrate the filtrate, recrystallize the residue from acetonitrile to give 2-[(1,2,3,4-tetrahydro-1-naphthyl)-methyl]-2-imidazoline hydrochloride, m.p. 195.5°-197° C.

EXAMPLE 3

2-[6,7,8,9-Tetrahydro-5H-5-benzocycloheptenylmethyl]-2-imidazoline maleate

Saturate a solution of 17.4 g. 5-cyanomethyl-6,7,8,9-tetrahydro-5H-benzocycloheptene and 10 ml. methanol in 100 ml. anhydrous ether with HCl at 0°. Keep at 0° for 3 days, add additional ether to precipitate the iminoether hydrochloride, and filter, m.p. 142°–143° C.

Add 19.8 g. iminoether hydrochloride to 350 ml. of an anhydrous ammonia-methanol solution and keep at room temperature 17 hours. Remove the methanol under reduced pressure and triturate the residue with ether to give the amidine hydrochloride.

Heat a solution of 13.4 g. amidine hydrochloride and 10.1 g. ethylenediamine in 100 ml. ethanol at reflux for 5 hours, cool the solution, add ethanolic HCl, and filter off the ethylenediamine dihydrochloride. Concentrate the filtrate, add 15% aqueous NaOH, and isolate the imidazoline with chloroform. Convert to the maleate salt to obtain 2-[6,7,8,9-tetrahydro-5H-5-benzocycloheptenylmethyl]-2-imidazoline maleate, m.p. 126.5°–128° C.

In a similar manner, by substituting the reactants of the foregoing examples with the required reactants, and by following substantially the same procedures so exemplified, there is produced the following compounds:

2-[(6-fluoro-1,2,3,4-tetrahydro-1-naphthyl)-methyl]-2-imidazoline;
2-[(5-fluoro-1,2,3,4-tetrahydro-1-naphthyl)-methyl]-2-imidazoline;
2-[(8-fluoro-1,2,3,4-tetrahydro-1-naphthyl)-methyl]-2-imidazoline;
2-[(6-fluoro-2-methyl-1,2,3,4-tetrahydro-1-naphthyl)-methyl]-2-imidazoline;
2-[(2-methyl-1,2,3,4-tetrahydro-1-naphthyl)-methyl]-2-imidazoline;
2-[(2-cyclopropyl-1,2,3,4-tetrahydro-1-naphthyl)-methyl]-2-imidazoline;
2-[1-indanylmethyl]-2-imidazoline;
2-[5-fluoro-1-indanylmethyl]-2-imidazoline;
2-[5-fluoro-2-methyl-1-indanylmethyl]-2-imidazoline;
2-[7-fluoro-1-indanylmethyl]-2-imidazoline;
2-[6,7,8,9-tetrahydro-5-H-5-benzocycloheptenylmethyl]-2-imidazoline;
2-[2-fluoro-6,7,8,9-tetrahydro-5H-5-benzocycloheptenylmethyl]-2-imidazoline;
2-[4-fluoro-6,7,8,9-tetrahydro-5H-5-benzocycloheptenylmethyl]-2-imidazoline;
2-[6-methyl-6,7,8,9-tetrahydro-5H-5-benzocycloheptenylmethyl]-2-imidazoline; and
2-[4-fluoro-6-methyl-6,7,8,9-tetrahydro-5H-5-benzocycloheptenylmethyl]-2-imidazoline.

Another aspect of this invention is a method of lowering blood sugar levels in warm-blooded animals. As stated above, the method of achieving this hypoglycemic effect in warm-blooded animals is achieved by administering a therapeutically effective quantity of a compound of the formula:

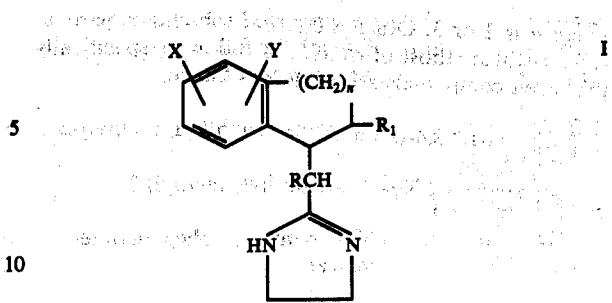

and the pharmaceutically acceptable acid addition salts thereof, wherein each of X and Y are hydrogen or fluoro, each of R and $R_1$ are lower alkyl or hydrogen, and $n$ is an integer 1 to 3. The therapeutically effective quantity of a compound of this invention (I) may readily be ascertained by standard and well-known techniques in the art. One such laboratory technique available to the attending diagnostician is the Alanine Induced Hyperglycemia assay wherein the effects of compound of the conversion of alanine to glucose (gluconeogenesis) is determined in normal $CF_1$ male mice, previously fasted for 18 hours, by administering the compound (or vehicle) by gavage one hour before the intraperitoneal administration of L-alanine (2 g./kg.). One hour after administration of alanine the mice are periodically bled and assayed for plasma glucose, lactate, and insulin. Test compounds may be compared against such standards as phenformin, tolazamide and insulin. This test, coupled, if desired, with other well-known assay techniques, e.g., the well-known acute and chronic glucose tolerance assays in genetic diabetic mice and the glucagon-induced hyperglycemia test in monkeys all afford ample evidence and basis for determining efficacy (both as to potency and profile) for the compounds of this invention. From these prior art test procedures, it is determined that the compounds of this invention, insofar as the hypoglycemic activity is concerned, are more potent than phenformin, they are active in genetic diabetic mice (sulfonylureas are not) with little or no tolerance to hypoglycemic effects, they prevent glucagon-induced hyperglycemia (in monkeys) and they have little likelihood of causing overt hypoglycemia. In addition to raising insulin levels in the standard test species, the compounds also increase insulin levels in genetic diabetic mice. In general, the compounds have no tolerance to insulinogenic effects and they increase insulin secretion in glucagon treated monkeys. The compounds also have little likelihood of increasing lactic acid levels. Thus, on an overall basis, it is determined that the compounds of this invention (I) have a therapeutically effective dose range of about 1 to 6 milligrams per kilogram of body weight (MPK) (particularly in warm-blooded animals having a 50 kg. body weight), preferably administered in three divided doses. In any given situation, however, the optimal therapeutic dosage for any given mammal suffering from diabetes may be established by the attending diagnostician using supplementary laboratory test procedures such as blood and urine analysis according to standard and well-known techniques.

As is true for most classes of therapeutically effective compounds, certain subclasses and specific compounds are found to be more effective than others. In this invention preferred groupings are those wherein the benzenoid moiety is substituted with a fluoro substituent, and when n is 2 or 3. Other preferred sub-classes particularly useful are those of which the following specifically preferred compounds are members thereof:

2-[(6-fluoro-1,2,3,4-tetrahydro-1-naphthyl)-methyl]-2-imidazoline;
2-[(1,2,3,4-tetrahydro-1-naphthyl)-methyl]-2-imidazoline; and
2-[(6,7,8,9-tetrahydro-5H-5-benzocycloheptenylmethyl]-2-imidazoline maleate.

In their functions as therapeutically useful compounds, it is advantageous to administer the compounds to the host animal in admixture with an acceptable pharmaceutical carrier suitable for enternal or parenteral administration, said carrier constituting a major portion of the admixture. Such preparations may be in such forms as, for example, tablets, capsules, and suppositories, or in liquid forms, as for example, elixirs, emulsions and injectables. In the formulations of pharmaceutical preparations there can be employed such substances which do not react with the active substance, as for example, water, gelatin, lactose, starches, magnesium stearate, talc, vegetable oils, benzyl alcohols, gums, polyalkylene glycols, petroleum jelly and the like. The active ingredient of such pharmaceutical preparations is preferably present in the preparations in such proportions by weight that the porportion by weight of the active ingredient to be administered lies between 0.1 and 50%.

TABLET FORMULATION

The following formulation provides for the manufacture of 1000 Tablets:

|   |   | Grams |
|---|---|---|
| (1) | 2-[6,7,8,9-tetrahydro-5H-5-benzocycloheptenylmethyl]-2-imidazoline maleate | 25.0 |
| (2) | Lactose, U.S.P. | 181.0 |
| (3) | Corn Starch, U.S.P. | 92.5 |
| (4) | Magnesium Stearate | 1.5 |

Thoroughly granulate a mixture of 72.5 g. of corn starch and the lactose with a paste prepared by dissolving 20 g. of corn starch in 100 ml. of hot distilled water. Dry the resulting granulation, add a blended mixture of the active ingredient (1) and the magnesium stearate. Thoroughly blend and then press into tablets of 300 mg. each.

CAPSULE FORMULATION

The following formulation provides for the manufacture of 1000 capsules:

|   |   | Grams |
|---|---|---|
| (1) | 2-[(1,2,3,4-tetrahydro-1-naphthyl)-methyl]-2-imidazoline hydrochloride | 25.0 |
| (2) | Lactose | 273.5 |
| (3) | Magnesium Stearate | 1.5 |

Mix active ingredient (1) with the lactose and blend in the magnesium stearate. Fill hard gelatin capsules with 300 mg. of each of the blended mixture to produce capsules containing 25 mg. of 2-[(1,2,3-tetrahydro-1-naphthyl)-methyl]-2-imidazoline hydrochloride.

PARENTERAL FORMULATION

The following formulation provides for the manufacture of 100 vials each containing 10 mg. of active ingredient, as the fumarate salt.

|   |   | Grams |
|---|---|---|
| (1) | 2-[6,7,8,9-tetrahydro-5H-5-benzocycloheptenylmethyl]-2-imidazoline maleate | 10.00 |
| (2) | Monobasic potassium phosphate | 6.00 |
| (3) | Water for injection, U.S.P., q.s. ad. 1.00 l. | |

Dissolve ingredients (1), (2), and (3) in approximately 80% of the volume of water and filter the resulting solution. Add to the filtrate sufficient water to bring up to volume. Sterile-filter the solution and aseptically fill one milliliter portions of the solution into two milliliter vials, then lyophilize. After the lyophilized cake is dry, aseptically stopper the vials with rubber plugs and seal.

I claim:
1. A method for eliciting a hypoglycemic effect in warmblooded animals having a hyperglycemic condition which comprises administering a therapeutically effective quantity of a compound of the structural formula:

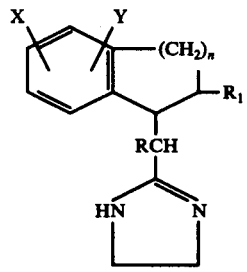

and the pharmaceutically acceptable acid addition salts thereof, wherein each of X and Y are hydrogen or fluoro, each of R and $R_1$ are lower alkyl or hydrogen, and n is an integer 1 to 3.

2. The method of claim 1 wherein n is 1.
3. The method of claim 1 wherein n is 2.
4. The method of claim 1 wherein n is 3.
5. The method of claim 2 wherein X is fluoro and Y, R and $R_1$ are hydrogen.
6. The method of claim 3 wherein X is fluoro, and Y, R and $R_1$ are hydrogen.
7. The method of claim 4 wherein X is fluoro, Y, R and $R_1$ are hydrogen.
8. The method of claim 2 wherein X, Y, R and $R_1$ are hydrogen.
9. The method of claim 3 wherein X, Y, R and $R_1$ are hydrogen.
10. The method of claim 4 wherein X, Y, R and $R_1$ are hydrogen.
11. The method of claim 1, said compound being 2-[1-(2-methyl-1,2,3,4-tetrahydronaphthyl)-methyl]-2-imidazoline hydrochloride.

* * * * *